(12) United States Patent
Mayo et al.

(10) Patent No.: US 12,178,925 B2
(45) Date of Patent: Dec. 31, 2024

(54) METHODS AND SYSTEMS FOR TREATMENT OF VEHICLE SURFACES AND AIR

(71) Applicants: Bryant Robert Mayo, Palmcoast, FL (US); Jerry Brower, Vancouver, WA (US); Terry John Grover, Parker, TX (US)

(72) Inventors: Bryant Robert Mayo, Palmcoast, FL (US); Jerry Brower, Vancouver, WA (US); Terry John Grover, Parker, TX (US)

( * ) Notice: Subject to any disclaimer, the term of this patent is extended or adjusted under 35 U.S.C. 154(b) by 553 days.

(21) Appl. No.: 17/074,421

(22) Filed: Oct. 19, 2020

(65) Prior Publication Data

US 2022/0118130 A1 Apr. 21, 2022

(51) Int. Cl.
*A61L 2/10* (2006.01)
*A61L 9/20* (2006.01)
*B60N 2/00* (2006.01)
*B60S 1/64* (2006.01)
*B62D 1/06* (2006.01)
(Continued)

(52) U.S. Cl.
CPC ...... *A61L 2/10* (2013.01); *A61L 9/20* (2013.01); *B60N 2/0021* (2023.08); *B60N 2/0025* (2023.08); *B60S 1/64* (2013.01); *B62D 1/06* (2013.01); *E05B 77/54* (2013.01); *A61L 2202/11* (2013.01); *A61L 2202/14* (2013.01); *A61L 2202/25* (2013.01); *A61L 2209/111* (2013.01); *B60N 2230/30* (2023.08); *G02F 1/13306* (2013.01); *G02F 1/172* (2013.01)

(58) Field of Classification Search
CPC .......... A61L 2/10; A61L 9/20; A61L 2202/11; A61L 2202/14; A61L 2202/25; A61L 2209/111; B60N 2/002; B60S 1/64; B62D 1/06; E05B 77/54; G02F 1/13306; G02F 1/172
See application file for complete search history.

(56) References Cited

U.S. PATENT DOCUMENTS

| 7,372,044 B2 | 5/2008 | Ross |
| 9,289,523 B2 | 3/2016 | Lee |

(Continued)

FOREIGN PATENT DOCUMENTS

| CN | 204932344 U | 1/2016 | |
| WO | WO-2019068189 A1 * | 4/2019 | ............... A61L 2/10 |

OTHER PUBLICATIONS

David Welch et al; Far-UVC light: A new tool to control the spread of airborne-mediated microbial diseases; Feb. 9, 2018; Nature Scientific Reports.

*Primary Examiner* — Regina M Yoo
(74) *Attorney, Agent, or Firm* — Derek Fahey, Esq.; The IP Plus Firm, PLLC

(57) ABSTRACT

The disclosure relates to systems and methods for treating a vehicle with radiation. The system generally comprises a being detection system, one or more sanitizing lights, a surface tinting means, and at least one processor. Sanitizing radiation is emitted onto one or more surfaces of the vehicle, as well as the air of the vehicle to sanitize the vehicle. The processor allows and being detection system allow for safe sanitizations to be conducted inside the vehicle. The vehicle may be treated with safe UV-C light and/or unsafe UV-C light, depending on the presence of beings in the vehicle.

6 Claims, 11 Drawing Sheets

(51) Int. Cl.
*E05B 77/54* (2014.01)
*G02F 1/133* (2006.01)
*G02F 1/17* (2019.01)

(56) References Cited

U.S. PATENT DOCUMENTS

| | | | |
|---|---|---|---|
| 9,522,201 | B2 | 12/2016 | Sunkara et al. |
| 9,550,006 | B2 | 1/2017 | Boodaghians et al. |
| 10,144,275 | B2 * | 12/2018 | Gaddis ................. G02F 1/0121 |
| 10,488,686 | B1 * | 11/2019 | Melcher .............. G02F 1/13306 |
| 10,556,027 | B2 | 2/2020 | Kreiner et al. |
| 10,843,535 | B1 * | 11/2020 | Mazuir ............... G02F 1/13725 |
| 2010/0241306 | A1 | 9/2010 | Akisada et al. |
| 2015/0253594 | A1 * | 9/2015 | Roberts ..................... B60J 3/04 |
| | | | 359/241 |
| 2016/0026061 | A1 * | 1/2016 | O'Keeffe ............ G02F 1/13394 |
| | | | 359/296 |
| 2016/0089459 | A1 | 3/2016 | Boodaghians et al. |
| 2017/0210352 | A1 | 7/2017 | Stauffer et al. |
| 2017/0283092 | A1 | 10/2017 | Brown et al. |
| 2018/0251122 | A1 | 9/2018 | Golston et al. |
| 2019/0383091 | A1 * | 12/2019 | Wilson .................... G09G 5/10 |
| 2020/0057421 | A1 | 2/2020 | Trikha et al. |
| 2020/0198445 | A1 | 6/2020 | Line et al. |
| 2020/0237940 | A1 | 7/2020 | Yan et al. |
| 2020/0331611 | A1 * | 10/2020 | Hack ........................ A61L 2/10 |
| 2021/0330837 | A1 * | 10/2021 | Hebeisen .................. E06B 9/42 |

* cited by examiner

METHODS AND SYSTEMS FOR TREATMENT OF VEHICLE SURFACES AND AIR

CROSS-REFERENCE TO RELATED APPLICATIONS

Not Applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present invention relates to the field of surface sanitizing treatment, and more specifically to the field of treating vehicle cabin surfaces and surrounding air.

BACKGROUND

The very nature of passenger transportation brings people into close proximity with one another inside a cabin of a vehicle. A passenger vehicle, regardless of whether it is a cab, train, car, bus, or plane, generally brings people together sharing cabin surfaces and cabin air. Often, the air inside the vehicle is recirculated within the cabin and multiple passengers will come in contact with the same surfaces and the same air. The proximate relationship between the passengers in the cabin and the points of contact to shared surfaces and air contributes to the spread of infectious diseases, viruses, and bacteria. The risk of transmission significantly increases within public transportation because passengers have been potentially exposed to viruses and bacteria from different points of unknown origin. Relatively, passengers who live together and travel together are generally exposed to similar viruses and bacteria on a daily basis.

Viruses and bacteria can spread through either droplet transmission, airborne transmission, direct contact, vector transmission such as a mosquito or insect, vehicle transmission such as food and raw meat, or a combination thereof. People, including passengers, often carry viruses and bacteria without showing any symptoms of disease or infection. With shared transportation (e.g., public transportation), where the passengers are usually unknown to one another, the passengers may be traveling knowingly sick, coughing and breathing, and touching shared surfaces all of which contribute to the spread of germs and disease.

Through the growth of technology and demand for ease of access, ride sharing applications and services are becoming increasingly popular. In fact, the Center for Disease Control publishes notices advising rideshare employees and passengers of necessary precautions to take to limit the spread of disease transmission. Recommendations to limit the spread of viruses and bacteria include social distancing, wearing a mask to slow airborne disease and prevent droplet transmission, and most importantly cleaning and disinfecting. In certain instances, some viruses may survive on surfaces from anywhere between a few minutes to a few hours, making disinfection of the vehicles cabin imperative to protect passengers. Current disinfection methods for surfaces, including hand cleaning through wipes and surface cleaners, are laborious, time consuming, costly, and only effective if every inch of the exposed surfaces subject to passenger contact is disinfected. Additionally, the air circulated between passengers within the vehicle's cabin is difficult to disinfect and often leads to contamination and thus the proliferation of disease.

As a result, there exists a need for improvements over the prior art and more particularly for a more efficient way of treating vehicle cabin surfaces and surrounding air.

SUMMARY

A system and method for treating a vehicle with radiation is disclosed. This Summary is provided to introduce a selection of disclosed concepts in a simplified form that are further described below in the Detailed Description including the drawings provided. This Summary is neither intended to identify key features or essential features of the claimed subject matter, nor is this Summary intended to be used to limit the claimed subject matter's scope.

In one embodiment, a system for treating a vehicle with radiation is disclosed. In one embodiment, the system comprises a being detection system, one or more sanitizing lights, a surface tinting means, and at least one processor. The being detection generally includes at least one sensor for sending a plurality of sensor signals. The sensor may be configured for sending the plurality of signals. The sensor signals are for indicating a presence of beings within at least one enclosed compartment of the vehicle. The one or more sanitizing lights include at least a first sanitizing light of a first type positioned to emit sanitizing radiation. The sanitizing radiation is emitted onto one or more surfaces of the vehicle, as well as the air of the vehicle (e.g., at least one compartment). The surface tinting means interacts with at least one window of the vehicle. A window tinting of the window (e.g., a state of the window tinting) is adjusted by the surface tinting means. In one embodiment, the surface tinting means adjusts the window tinting between a safe shade and an unsafe shade (e.g., relative to safe UV-C light and unsafe UV-C light). The safe shade prevents harmful radiation from passing through the window(s).

The at least one processor may be used for (e.g., configured for) (1) receiving the plurality of sensor signals from the being detection system, (2) processing the plurality of sensor signals from the being detection system, (3) sending deactivation signals to the first sanitizing light to power-off the first sanitizing light, (4) sending activation signals to the first sanitizing light to power-on the first sanitizing light, and (5) sending tinting signals to the surface tinting means to adjust the window tinting. The processing the plurality of sensor signals (2) is generally for determining a probability of a presence of beings within the at least one enclosed compartment. The methods for determining that presence are discussed in greater detail below.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein.

DETAILED DESCRIPTION

Figure 1A:
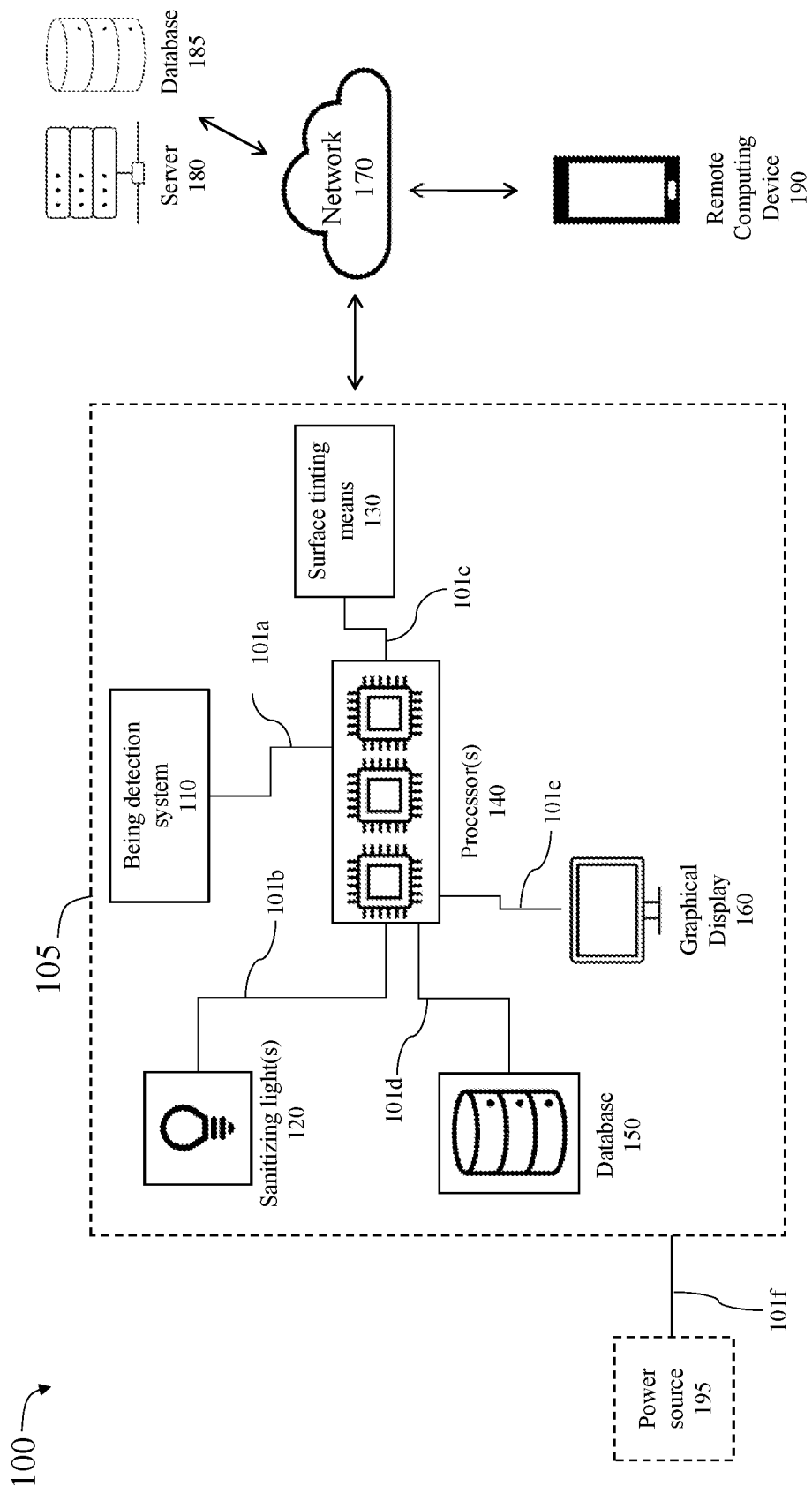
FIG. 1a is a diagram of system in an environment for treating a vehicle, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a system and method for treating passenger transportation vehicle cabin surfaces and surrounding air. The disclosed systems and methods improve over the prior art by enabling safe sanitization of the vehicle, regardless if beings are present inside the vehicle or not. The safety of the sanitization extends to outside the vehicle, where beings are protected from harmful rays by selectively tinting window(s) of the vehicle. Lastly, the disclosed systems and methods improve over the prior art by automating the sanitization process and enabling the user to, in real-time, monitor the sanitary conditions of the vehicle.

The term, "vehicle" refers to an object for transporting, among other things, people from one location to another. Non-limiting examples of vehicles includes automobiles, buses, trains, planes, and spaceships, among others.

In one embodiment, a system for treating a vehicle having at least one enclosed compartment with radiation, wherein the system comprises: (a) a being detection system having at least one sensor configured for sending a plurality of sensor signals, wherein the plurality of sensor signals indicate a presence of beings within the at least one enclosed compartment, (b) one or more sanitizing lights, wherein the system comprises at least a first sanitizing light of a first type positioned to emit sanitizing radiation on one or more surfaces and air within the at least one enclosed compartment, (c) a surface tinting means interacting with at least one window of the vehicle, wherein the at least one window has a window tinting, wherein the surface tinting means adjusts the window tinting between a safe shade and an unsafe shade, wherein the safe shade prevents harmful radiation from passing through the at least one window, (d) at least one processor, wherein the at least one processor is configured for: (i) receiving the plurality of sensor signals from the being detection system, (ii) processing the plurality of sensor signals from the being detection system to determine a probability of a presence of beings within the at least one enclosed compartment, (iii) sending deactivation signals to the first sanitizing light to power-off the first sanitizing light, (iv) sending activation signals to the first sanitizing light to power-on the first sanitizing light, and, (v) sending tinting signals to the surface tinting means to adjust the window tinting.

In another embodiment, a system for treating a vehicle having at least one enclosed compartment with radiation, wherein the system comprises: (a) a being detection system having at least one sensor configured for sending a plurality of sensor signals, wherein the plurality of sensor signals indicate a presence of beings within the at least one enclosed compartment, (b) one or more sanitizing lights, wherein the system comprises at least a first sanitizing light of a first type and a second sanitizing light of a second type positioned to emit sanitizing radiation on one or more surfaces and air within the at least one enclosed compartment, wherein sanitizing lights of the first type emit first sanitizing radiation and wherein sanitizing lights of the second type emit second sanitizing radiation, wherein the first sanitizing radiation includes unsafe UV-C radiation and the second sanitizing radiation includes safe UV-C radiation and excludes unsafe UV-C radiation, (c) a surface tinting means interacting with at least one window of the vehicle, wherein the at least one window has a window tinting, wherein the surface tinting means adjusts the window tinting between a safe shade and an unsafe shade, wherein the safe shade prevents harmful radiation from passing through the at least one window, (d) at least one graphical display displaying a report, wherein the report displays at least one of a presence of beings within the vehicle, a degree of tinting for the at least one window, an expected remaining lifetime of the one or more sanitizing lights, and a period of time since a sanitization has occurred, (e) at least one processor, wherein the at least one processor is configured for: (i) receiving the plurality of sensor signals from the being detection system, (ii) processing the plurality of sensor signals from the being detection system, wherein the processing comprises: determining a probability of a presence of beings within the at least one enclosed compartment, preparing the report, (iii) sending deactivation signals to the at least one of the first sanitizing light and the second sanitizing light to power-off at least one of the first sanitizing light and the second sanitizing light, (iv) sending activation signals to the at least one of the first sanitizing light and the second sanitizing light to power-on at least one of the first sanitizing light and the second sanitizing light, (v) sending tinting signals to the surface tinting means to adjust the window tinting, (vi) sending display signals comprising the report to the at least one graphical display. In one embodiment, the one or more sanitizing lights comprises a second sanitizing light of a second type, wherein sanitizing lights of the first type emit first sanitizing radiation and sanitizing lights of the second type emit second sanitizing radiation, wherein the first sanitizing radiation is different from the second sanitizing radiation.

In one embodiment, the sending activation signals comprises sending the activation signals to at least one of the first sanitizing light and the second sanitizing light to power-on at least one of the first sanitizing light and the second sanitizing light.

In one embodiment, the first sanitizing radiation includes unsafe UV-C radiation (defined below), and wherein the second sanitizing radiation includes safe UV-C radiation (defined below) and excludes unsafe UV-C radiation.

In one embodiment, the one or more sanitizing lights comprises at least one ultraviolet radiation source. In one embodiment, the at least one ultraviolet radiation source emits at least some unsafe UV-C radiation. In one embodiment, the at least one ultraviolet radiation source emits at least some safe UV-C radiation.

Various references to the terms, "rays," "electromagnetic radiation," "radiation," and "light" are used herein and those terms are used interchangeably.

i. System Components

Figure 1B:
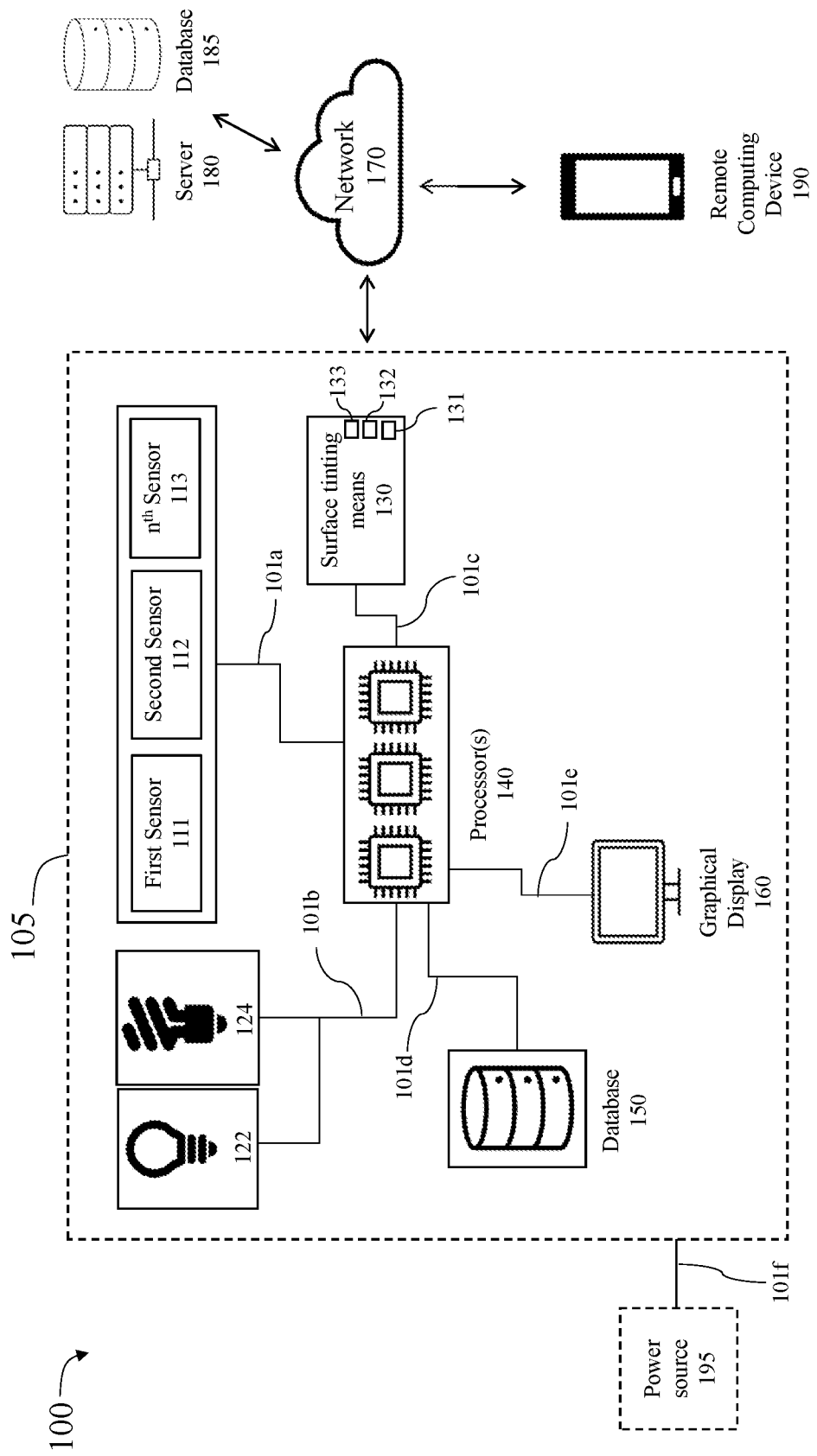
FIG. 1b is a diagram of a more particular system in an environment for treating a vehicle, according to an example embodiment.

Referring now to FIGS. 1a-1b, an embodiment of a system for treating a vehicle with radiation is disclosed. The system 100 comprises a being detection system 110, one or more sanitizing lights 120, a surface tinting means 130, and at least one processor 140. The being detection system 110 generally includes at least one sensor (111, 112, 113) for sending a plurality of sensor signals (illustrated in FIG. 4). The processor is generally connected, either directly (e.g., via electrical connection) or indirectly (e.g., via a network) to the system components. The system also may comprise a graphical display 160 for displaying a report. As illustrated, the system components shown within the boundaries of the vehicle 105 are connected electrically via a plurality of conductors (101a-101f). The plurality of conductors may be, for instance, a plurality of wires.

The aforementioned components (110-160) may also be connected to one or more power sources 195. The power source is shown, for convenience, as being connected to the vehicle boundary 105 but is understood as meaning the power source 195 is connected with these components (110-160). The power source(s) may include an external battery, a battery of the vehicle (e.g., the same battery used to start the vehicle), a power generator within the vehicle (e.g., an alternator inside the vehicle's engine), and combinations thereof, among others.

The components within the vehicle boundary 105 may be wirelessly connected to a network 170. Network 170 may include one or more packet switched networks, such as the Internet, or any local area networks, wide area networks, enterprise private networks, cellular networks, phone networks, mobile communications networks, or any combination thereof.

The network 170 may be connected to a server 180, a database 185, and a remote computing device 190 (e.g., a remote computing device of a vehicle's user(s)). Server 180 includes a software engine that delivers applications, data, program code and other information to at least the computing device 190 and to the processor(s) 140. The software engine of server 180 may perform other processes such as transferring multimedia data in a stream of packets that are interpreted and rendered by a software application as the packets arrive. Database 180 may be one of a relational database comprising a Structured Query Language (SQL) database stored in a SQL server or a database that adheres to the NoSQL paradigm. Multiple databases may be used, and each database may utilize its' own data paradigm.

The remote computing device 190 may be any suitable remote computing device, such as a cellular telephone (e.g., IPHONE®, ANDROID®), tablet (e.g., IPAD®), smart phone or any other mobile device. Other suitable remote computing devices may also include laptops and gaming consoles, for example.

Further details for each of the components of the system 100 are described in greater detail below.

a. Sanitizing Light(s)

As noted above and with continued reference to FIGS. 1a-1b, the system 100 includes sanitizing light(s) 120, such as a first sanitizing light 122. Generally, all sanitizing light(s) 120 are positioned to emit sanitizing radiation into the vehicle, whether that may be to a particular compartment or throughout the cabin of the vehicle. The sanitizing lights may be integrated into the vehicle, or the lights may be affixed (e.g., installed) into the vehicle, and any combinations thereof.

A plurality of lights and light types may be used. For instance, the first sanitizing light 122 may of a first type. A second sanitizing light 124 of a second type may also be used. In this regard, n-number of lights and n-number types of lights may be used. Regardless of the number of sanitizing lights and the number of types of lights used, the sanitizing radiation is emitted onto one or more surfaces of the vehicle, as well as the air of the vehicle (e.g., at least one compartment). Depending on the circumstances, the preferred type of light emits unsafe UV-C light or safe UV-C light. The type of light used generally depends on whether or not beings are present in the vehicle.

The term, "sanitizing light type" refers to a particular type of a sanitizing light, where the particular type of light is defined by the intensity and spectrum of the radiation emitted by the sanitizing light. For instance, a light that emits radiation at a wavelength of 180±1 nanometers is a different type of light than a light that emits radiation at a wavelength of 222±1 nanometers. However, other embodiments may be used and are within the spirit and scope of the present invention.

The term, "UV-C" radiation refers to electromagnetic radiation having a wavelength from 100 to 280 nanometers. The term, "UV" refers to "ultraviolet." Thus, the term, "UV-C" radiation refers to the C-band of ultraviolet electromagnetic radiation. As known to those skilled in the art, ultraviolet electromagnetic radiation (ultraviolet light for short) includes three bands, UV-A, UV-B, and UV-C. The UV-A band is positioned at the longer wavelength side of the ultraviolet light spectrum, and UV-A light is the lowest energy ultraviolet light of the three bands. The UV-C band is positioned at the shorter wavelength side of the ultraviolet light spectrum, and UV-C light is the highest energy ultraviolet light of the three bands. UV-B is an intermediate energy and intermediate wavelength between the UV-A and UV-C bands. The surface of the earth does not receive a significant amount of UV-C radiation from the sun because the ozone layer blocks this wavelength of radiation.

The term, "safe UV-C radiation" refers to UV-C radiation having a wavelength of at least 200 nanometers. The term, "safe" refers to the safety of the electromagnetic radiation exposure to human beings. In other words, safe UV-C radiation is electromagnetic radiation having a wavelength from 200 to 280 nanometers. In one embodiment, safe UV-C radiation is electromagnetic radiation having a wavelength from 200 to 250 nanometers. In another embodiment, safe UV-C radiation is electromagnetic radiation having a wavelength from 210 to 235 nanometers. In yet another embodiment, safe UV-C radiation is electromagnetic radiation having a wavelength from 215 to 225 nanometers. In one embodiment, safe UV-C radiation is electromagnetic radiation having a wavelength of approximately 222 nanometers (e.g., 220 to 224 nanometers).

The term, "unsafe UV-C radiation" refers to electromagnetic radiation having a wavelength of less than 200 nanometers. In other words, unsafe UV-C radiation is electromagnetic radiation having a wavelength from 100 to less than 200 nanometers. In one embodiment, an unsafe UV-C radiation treatment includes exposing the light to the inside of a vehicle for at least 5 minutes. In another embodiment, an unsafe UV-C radiation treatment includes exposing the light to the inside of a vehicle for at least 10 minutes. In yet another embodiment, an unsafe UV-C radiation treatment includes exposing the light to the inside of a vehicle for at least 15 minutes.

The type of lights that may be used include low pressure mercury lamps, low pressure amalgam lamps, medium pressure ultraviolet lamps, quartz sleeve lamps, and light emitting diodes ("LED"). LED lights may be preferred for the ability to emit electromagnetic radiation on a much narrower spectrum (e.g., ±1 nanometers). The ability to emit radiation on such a narrow spectrum allows for an increased predictability of the safety.

b. Surface Tinting Means

The surface tinting means 130 interacts with at least one window of the vehicle. A window tinting of the window (e.g., a state of the window tinting) is adjusted by the surface tinting means. In one embodiment, the surface tinting means 130 adjusts the window tinting between a safe shade and an unsafe shade (e.g., relative to safe UV-C light and unsafe UV-C light). The safe shade prevents harmful radiation (e.g., unsafe UV-C light) from passing through the window(s).

The term, "unsafe shade" refers to a shade that unsafe radiation can penetrate. The term, "safe shade" refers to a shade that blocks at least 95% of unsafe radiation from penetrating. Unsafe radiation may be, for instance, unsafe UV-C light. In one embodiment, a safe shade blocks at least 97% of unsafe radiation from penetrating. In another embodiment, a safe shade blocks at least 99% of unsafe radiation from penetrating. In yet another embodiment, a safe shade blocks at least 99.9% of unsafe radiation from penetrating.

A tinted shade (e.g., a safe shade) may also block a substantial amount of visible light. Blocking visible light may be useful for privacy purposes. For instance, at night time the system may conduct sanitizations. During the sanitization, the interior of the vehicle may be illuminated by the radiation, and this may be of concern for preventing theft. However, the tinted shade may prevent any thieves from viewing the inside of the vehicle.

Any means for tinting known in the art may be used for tinting at least one window of a vehicle. In one embodiment, the surface tinting means comprises an electrochromic device. An electrochromic device (e.g., a coating) comprises at least one layer of electrochromic material that exhibits a change from one optical state to another optical state, based on a change in voltage applied to the device. Any suitable electrochromic device may be used, such as one or more of a liquid crystal device, a suspended particle device, and a microelectromechanical ("MEM"S) device. The term, "liquid crystal device" refers to a device that incorporates liquid crystals (e.g., between two panes of glass) to change the optical state. The term, "suspended particle device" refers to a device that incorporates suspended particles to change the optical state. The term, "microelectromechanical device" refers to a device that incorporates microelectromechanical systems to change the optical state.

In another aspect of the invention, multi-layered windows that incorporate surface tinting means 130 are contemplated. For instance, as shown in FIG. 5d, a multi-layered window 550 is shown. As illustrated, the multi-layered window has a first layer 560, second layer 570, and a third layer 580. In one example, the first layer 560 is a glass window, the second layer 570 is a tinted layer, such as a surface tinting means layer, and the third layer 580 is a display layer. The surface tinting means layer 570 may be any one of the aforementioned surface tinting means described above. Furthermore, the third layer 580 may function as a graphical display, allowing the user to display, inter alia, a report (described in greater detail below). In one embodiment, the graphical display layer 580 may be used as a sanitizing light. Furthermore, an additional layer may be used that emits sanitizing radiation and is considered a sanitizing light.

Embedded lights (e.g., embedded LED lights) may also be used in one or more windows in the vehicle. For instance, a plurality of embedded lights 581 may be installed into the third layer 580. The embedded lights 581 may also be embedded into any of the first layer 560 and second layer 570.

As noted above, the present invention generally includes a surface tinting means 130. However, as one skilled in the art may appreciate, other means for providing a barrier that is generally impenetrable by unsafe radiation (greater than 95%) may be used. For instance, a motorized drawn shade may also be used, the drawn shade comprising at least one motor 131 for moving the shade between a collapsed configuration and an expanded configuration, and at least one sensor for detecting the shade's position 132, both the motor(s) and sensor(s) being in electrical communication with the processor(s) 140 and power source 195. The drawn shade also comprising shade 133. In this way, a drawn shade may effectively be used a surface "tinting" means. Thus, in some embodiments, a drawn shade is used as a surface tinting means 130 as described above.

c. The Being Detection System

As noted above, the system generally includes a being detection system. The being detection system 110 may be comprised of a plurality of sensors (111, 112, 113) in electrical communication with the processor(s) 140. For instance, sensor(s) (111, 112, 113) may be configured for sending a plurality of signals. Generally, the sensor signals are for indicating a presence of beings within the vehicle. A variety of methods (e.g., algorithms) may be used to determine a presence of beings. For instance, an activated (or deactivated) sensor signal may positively indicate a presence of beings, and a probability of presence of beings may be adjusted. Based on a minimum probability threshold, a presence of beings can be determined.

Other algorithms may also be used. For instance, a point system may be used. Each sensor may contribute one or more points to the sum total of points and each sensor may have a weighted value to contribute to the sum total of points (e.g., a seat sensor contributes 1 point, a steering wheel sensor contributes 5 points). Based on a minimum point threshold, the presence of beings in a vehicle may be determined. In yet another embodiment, an algorithm may be used in which every possible combination of activated/deactivated sensor signals corresponds to a binary outcome, i.e., whether or not beings are present in the vehicle. Other methods (e.g., algorithms) not discussed here that are known in the art may also be used.

Determining the presence of beings in the vehicle may influence what type of sanitization to apply to the vehicle, depending on numerous factors (described below). The sensor(s) may send the signals via one or more of electrical communication and wireless communication (e.g., Bluetooth, Wi-Fi). In one embodiment, electrical communication provided by a plurality of wires is used.

A variety of sensors (111, 112, 113) may be included in the being detection system 110. With reference now to FIGS. 1a-1b and FIG. 2b, for instance, in one embodiment, a being detection system 110 comprises at least one of a seat sensor 311, a seatbelt sensor 312, a door sensor 313, a steering wheel sensor 314, a window sensor 315, an infrared light signal 316, and a daylight sensor (not illustrated, described in greater detail below). These types of sensors, and how they may influence algorithms for determining sanitization protocols are described in greater detail below.

With reference now specifically to FIG. 2b, a variety of seat sensors 311 may be used to sense attribute(s) associated with the vehicle. In one embodiment, a seat sensor 311 interacts with an upward facing surface of a seat within the vehicle. The seat sensor(s) 311 may be located within one or more of the seats in the vehicle. Generally, a seat sensor 311 is capable of detecting if a being is positioned on the seat. A variety of sensors may be used, for instance conductivity sensors, and piezoelectric sensors, among others. Any other type of sensor known in the art may be used. A seat sensor signal may communicate data to the being detection system 110. For instance, the data may be binary data (e.g., a yes/no if the sensor is activated). The data may also be non-binary, including multiple measurements, for instance, (1) a yes/no signal if the sensor is activated in combination with (2) the total weight of the being or object that activated the signal. For determining if beings are present in a vehicle, an activated seat sensor modifies the probability of a presence of beings. In one embodiment, an activated seat sensor increases the probability to 70%, or higher, that a being is present in the vehicle.

Seatbelt sensor(s) 312 may be included. A seatbelt sensor is generally capable of sensing if a seatbelt is in a buckled position. Any seatbelt sensor known in the art may be used. Signals sent from the seatbelt sensor(s) may be binary (e.g., a yes/no corresponding to the buckling position). A seatbelt may be engaged without a user being present in the vehicle. Thus, a seatbelt sensor may modify the probability of a presence of beings modestly (e.g., increase by 10% or more). However, in conjunction with one or more other activated sensors (e.g., seat sensor), an activated seatbelt sensor may modify the probability more substantially (e.g., increase by 20% or more).

Door sensor(s) 313 may be included. A door sensor 313 generally detects if at least one door of the vehicle (e.g., driver door, passenger door(s)) is in an open position. Any door sensor known in the art may be used. A door sensor 313 does not directly detect if a being is present in a vehicle. Rather, a door sensor 313 being activated may be interpreted in a variety of ways. For instance, a human being may be about to enter the vehicle or may be exiting the vehicle. Harmful rays (e.g., unsafe UV-C radiation) may escape the vehicle if a sanitizing protocol is initiated while one or more doors are open. Thus, an activated door sensor in some embodiments modifies the probability of a presence of beings to 100%.

The door(s) may include a lock having an unlocked state and a locked state. In In one embodiment, the lock is in the locked state when a light is on a powered-on state and emitting radiation. Locking the vehicle may increase user safety. For instance, a user may try to enter into a vehicle while harmful rays are being emitted from the sanitizing light(s). In this way, unlocking the vehicle would modify the probability of a presence of beings (e.g., to 100%) and any unsafe radiation emission may be halted.

A steering wheel sensor 314 may be included. Any steering wheel sensor known in the art may be used. A steering wheel sensor is generally capable of detecting if a being (e.g., user of the vehicle) has engaged the steering wheel. An activated steering wheel is generally interpreted as a 100% probability that a being is in the vehicle.

Window sensor(s) 315 interacting with the window(s) may be included. Any window sensor known in the art may be used. A window sensor generally is capable of detecting if a window of the vehicle is open (e.g., partially, or fully open). Harmful rays (e.g., unsafe UV-C radiation) may escape the vehicle if a sanitizing protocol is initiated while one or more windows have been lowered. Thus, similarly to the door sensor(s) 313, an activated window door sensor may modify the probability of a presence of beings to 100% to prevent harmful rays from escaping the vehicle.

Infrared light sensor(s) 316 may be included (e.g., mounted in the vehicle). Any infrared light sensor known in the art may be used. An infrared light sensor 316 may be used to determine if a being is present by detecting an infrared signature. Infrared electromagnetic radiation may be used to determine the temperature of the field being measured. In this regard, the temperature associated with the temperature of the human body (e.g., approximately 98 degrees Fahrenheit) may be measured. The temperature of other beings, such as human pets (e.g., dogs, cats) may also be measured. Accordingly, an infrared signature may provide a variable modification of the probability of a presence of beings (e.g., between 30 and 100%), depending on how closely the detected signature matches a standardized signature.

A daylight sensor may also be used. A daylight sensor is generally capable of detecting if the vehicle is being exposed to sunlight (or if the vehicle should be exposed to sunlight, absent barriers of the sunlight). A daylight sensor may be comprised of a plurality of sensors. For instance, some commercial vehicles utilize a daylight sensor, and the intensity of light being emitted from the headlights of the vehicle is adjusted based on the time of day. Such daylight sensors present in commercial vehicles may be incorporated into the invention described herein. Further sensors may be used to form what is considered a daylight sensor. For instance, a global position system ("GPS") may be used to determine the location of a user's vehicle. Based on the measurement of the user's vehicle location (e.g., latitude and longitude), the time of day of the vehicle may be determined. In this way, several sensors may make up the daylight sensor.

In some instances, the signals from the daylight sensor are not used to determine the probability of the presence of a being. Rather, the daylight sensor may be used to determine if it is safe to power-on lights inside the vehicle. For instance, it may be dangerous to have lights emitting radiation while a user is driving if there is an absence of daylight (e.g., making it difficult for the driver to see the road). In this example, the daylight sensor can be used programmatically to avoid the condition where sanitizing lights are powered-on inside the vehicle while it is dark out. Similarly, certain barriers may prevent light from shining through the vehicle, for example when traveling through a tunnel. In this example, the daylight sensor can detect the change in daylight and power-off the sanitizing light(s). Thus, the daylight sensor may be used to programmatically influence sanitizing protocols to ensure user safety of the vehicle during operation.

d. Processor(s)

As noted above, the system also comprises at least one processor 140. The processor(s) 140 may be used for (e.g., configured for) (1) receiving the plurality of sensor signals from the being detection system, (2) processing the plurality of sensor signals from the being detection system, (3) sending deactivation signals to the first sanitizing light to power-off the first sanitizing light, (4) sending activation signals to the first sanitizing light to power-on the first sanitizing light, and (5) sending tinting signals to the surface tinting means to adjust the window tinting. The processor(s) 140 may be in electrical communication with each of the system components described above, e.g., by way of a plurality of conductors (101a-101f). The processing the plurality of sensor signals (2) is may include determining a probability of a presence of beings within the at least one enclosed compartment. The algorithmic methods for determining that presence are discussed in greater detail below.

As noted above, the processor(s) is/are generally connected to the components of the system (110-130, 150-160), and optionally being connected to a network 170 and devices associated with the network (180-190). Each of the sensors of the being detection system 110 are capable of sending signals to the at least one processor. Thus, in one embodiment, at least one of the seat sensor, the seatbelt sensor, the door sensor, the steering wheel sensor, the daylight sensor, the window sensor, and the infrared light sensor are capable of sending at least some of the plurality of sensor signals to the at least one processor. The sensor signals communicate data (e.g., binary data, non-binary data) to the processor, and the processor may be programmed to calculate a probability of a presence of beings based on the data provided by the sensor(s). The probability of a presence of beings is therefore a function of all of the received sensor data. Thus, In one embodiment, the probability of a presence of beings is a function of the plurality of sensor signals from at least one of the seat sensor, the seatbelt sensor, the door sensor, the steering wheel sensor, the daylight sensor, the window sensor, and the infrared light sensor.

Figure 4:
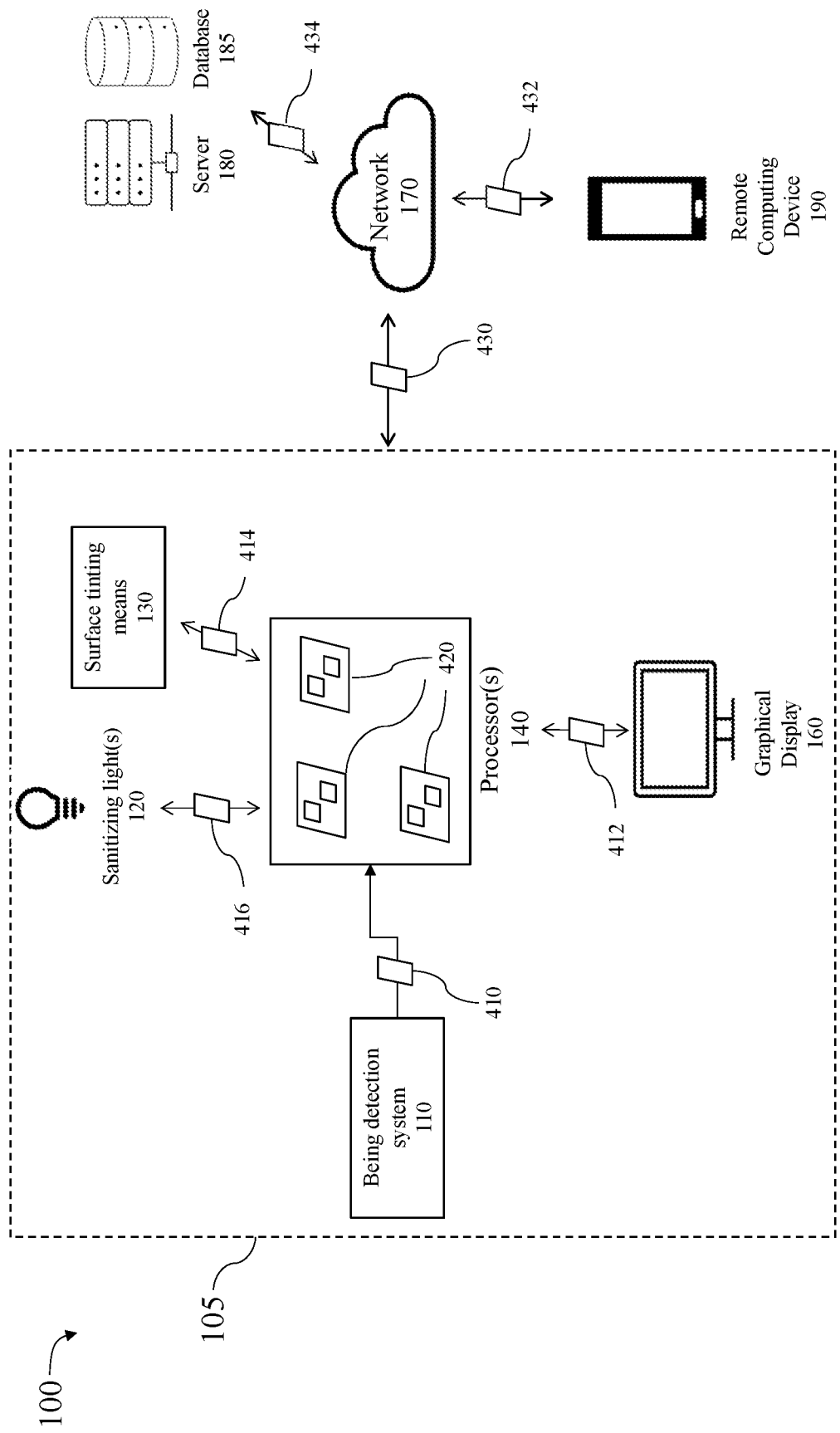
FIG. 4 is a diagram of a system in an environment for treating a vehicle, illustrating the transmission of signals between the system components, according to an example embodiment.

Referring now to FIG. 4, a diagram showing the flow of data within system 100 is shown. Components within the vehicle 105 are shown within the dotted-line boundary. As illustrated, signals 410 from the being detection system 110 are sent to the processor(s) 140. Signals 410 from the being detection system 110 generally include data from the sensor(s) associated with the being detection system 110. The data being transmitted via the signals 410 can be binary or non-binary data. Regardless, the signals 410 are processed by the processor(s) 140 to determine a probability of a presence of beings within the vehicle. After determining the probability of a presence of beings, the processor(s) 140 may transmit signals to, and from, the sanitizing light(s) 120, the surface tinting means 130, the graphical display 150, and/or the network 170.

After determining a presence of beings, the processor(s) may prepare a plurality of data 420 to send to the other components of the system via signals (412, 414, 416, 430). For instance, the processor(s) may send light signals 416 to the sanitizing light(s) 120. The light signals 416 may be activation signals to power-on the light(s) 120, or the light signals 416 may be deactivation signals to power-off the light(s) 120. Similarly, tinting signals 414 may be sent to the surface tinting means 130. The tinting signals 414 may adjust the window tinting of at least one window. For instance, the tinting signals 414 may adjust the tinting of at least one window to one of a safe shade, or an unsafe shade (defined above).

Display signals 412 may be sent from the processor(s) 140 to the graphical display 160. The display signals 412 may include a report to be displayed on the graphical display 160. Similarly, the report may be sent via network signals 430 to the network 170 to be sent to a remote computing device 190 via remote computing signals 432. Accordingly, the report can also be displayed on the remote computing device 190. The data that may be included in the report is described in greater detail below.

System 100 is shown as being connected to a network 170 (e.g., the internet). It is to be understood that the processor(s) 140 may send data to the network 170 directly (e.g., via wireless connection), and/or indirectly by first sending signals from the processor(s) 140 to the remote computing device 190 (e.g., via BLUETOOTH®), and from the remote computing device 190 to the network 170.

The network 170 may send server signals 434 to a server and/or database (180, 185). The database 185 may include a catalog of data collected by the being detection system. Furthermore, remote computing signals 432 may be sent to remote computing device 190. Moreover, the processor(s) 140 may be directly connected to a local database (not illustrated on FIG. 4) and a catalog of data collected by the being detection may be stored on the local database.

Figure 6:
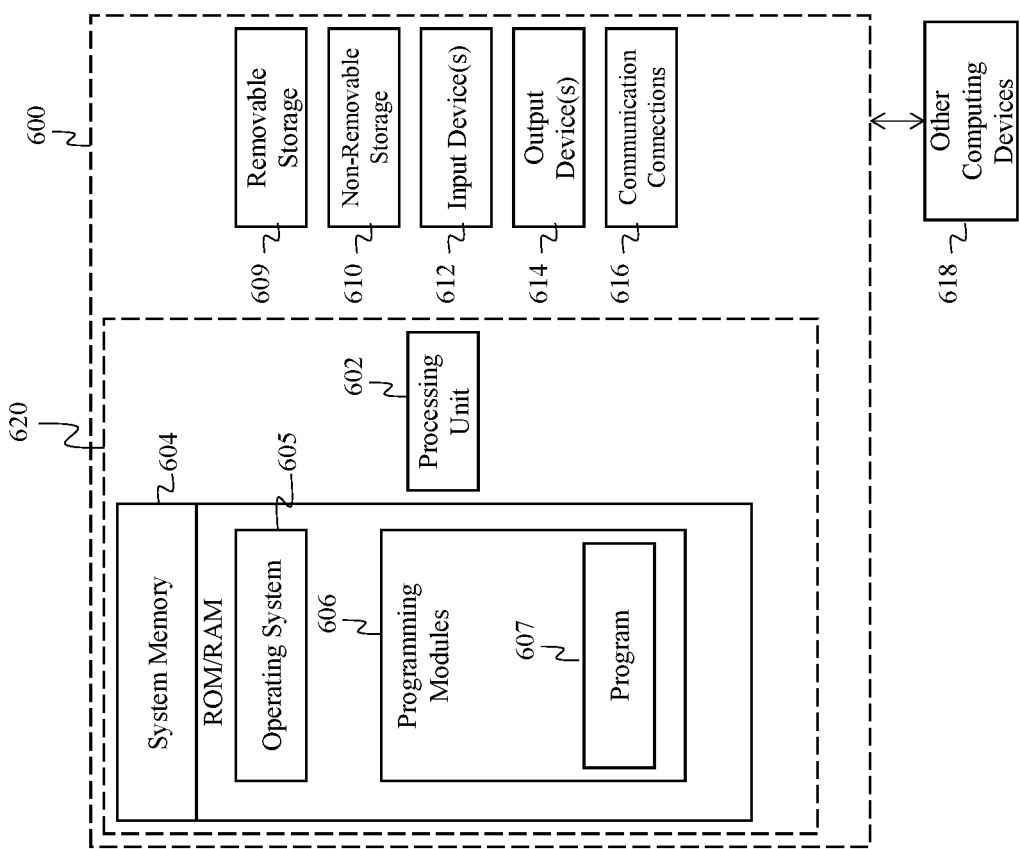

Each of the processor(s) 140 may be included as a part of a computing device or may also be a device performing some or all of functions of a computing device. Referring now to FIG. 6, a computing device 600 is shown. FIG. 6 is a block diagram of a system including an example computing device 600 and other computing devices. Consistent with the embodiments described herein, the aforementioned actions performed by the processor(s) 140, servers 180, remote computing device 190, etc., may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise or be included in the operating environment (e.g., shown by system 100) and processes and dataflow as described above. However, processes described above may operate in other environments and are not limited to computing device 600.

With reference now to FIG. 6, a block diagram of a system including an example computing device 600 and other computing devices is shown. Consistent with the embodiments described herein, the aforementioned actions may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for system 100. Processes, data related to system 100 may operate in other environments and are not limited to computing device 600.

A system consistent with an embodiment of the invention may include a plurality of computing devices, such as computing device 600. In a basic configuration, computing device 600 may include at least one processing unit 602 (i.e., processor(s) 140 described above) and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of system 100. Furthermore, embodiments of the invention may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable, and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of system 600. Computing device 600 may also have input device(s) 612 such as a keyboard, a mouse, a pen, a sound input device, a camera, a touch input device, etc. Output device(s) 614 such as a display, speakers, a printer, etc. may also be included. The aforementioned devices are only examples, and other devices may be added or substituted.

Computing device 600 may also contain a communication connection 616 that may allow system 100 to communicate with other computing devices 618, such as over a network 170 in a distributed computing environment, for example, an intranet or the Internet. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g., program module 607) may perform processes including, for example, one or more of the stages of a process. The aforementioned processes are examples, and processing unit 602 may perform other processes. The aforementioned processes are examples, and processing unit 602 may perform other processes and may also be configured to provide graphical user interfaces displayed associated with devices explained above. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages, and/or inserting or deleting stages, without departing from the invention.

e. Graphical Displays

With reference now back to FIGS. 1a-1b, in one embodiment, the at least one processor 140 is configured for generating a report and displaying it on a display (e.g., remote computing device 190, graphical display 160). The report may provide the user with an entertainment experience. Moreover, the graphical display 160 of the report may inform the user about the sanitary conditions in the vehicle, light-bulb conditions, etc. In one embodiment, the report comprises at least one of a presence of beings within the vehicle, a degree of tinting for the at least one window, an expected remaining lifetime of the one or more sanitizing lights, and a period of time since a sanitization has occurred.

Figure 5A:
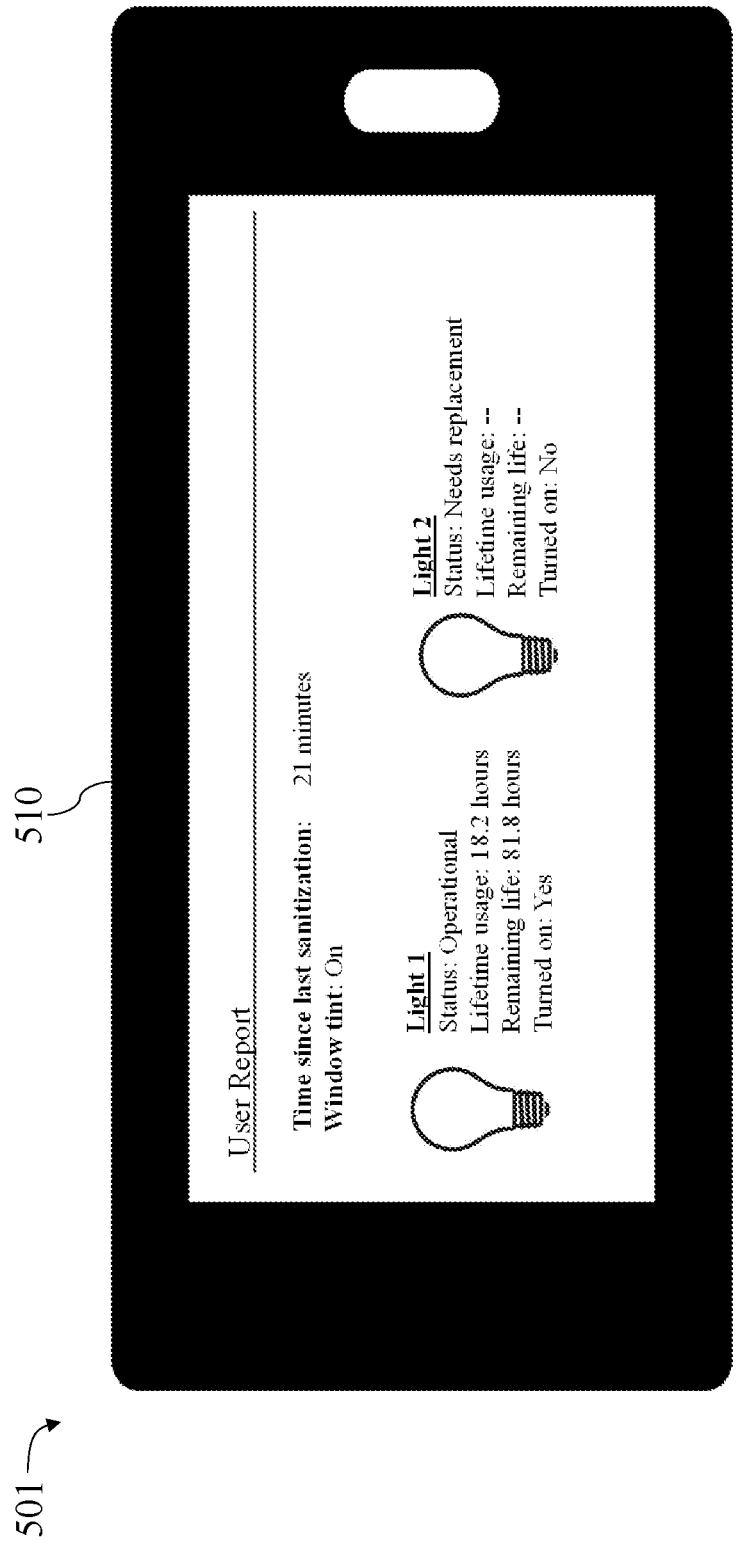
FIG. 5a is an embodiment of a graphical user interface of user report, according to an example embodiment.

Referring now to FIG. 5a an embodiment of a report 501 illustrated on a graphical display 510 is shown. As illustrated, the report informs the user of: the time since the last sanitization, the status of the window tint, and information regarding two lights in the vehicle. As illustrated, light #1 is operational and the estimated remaining life of the lightbulb is calculated based on an estimated 100-hour bulb lifetime. Conversely, light #2 needs replacement. Since light #1 is operational, the window tint in the vehicle is turned on.

Figure 5B:
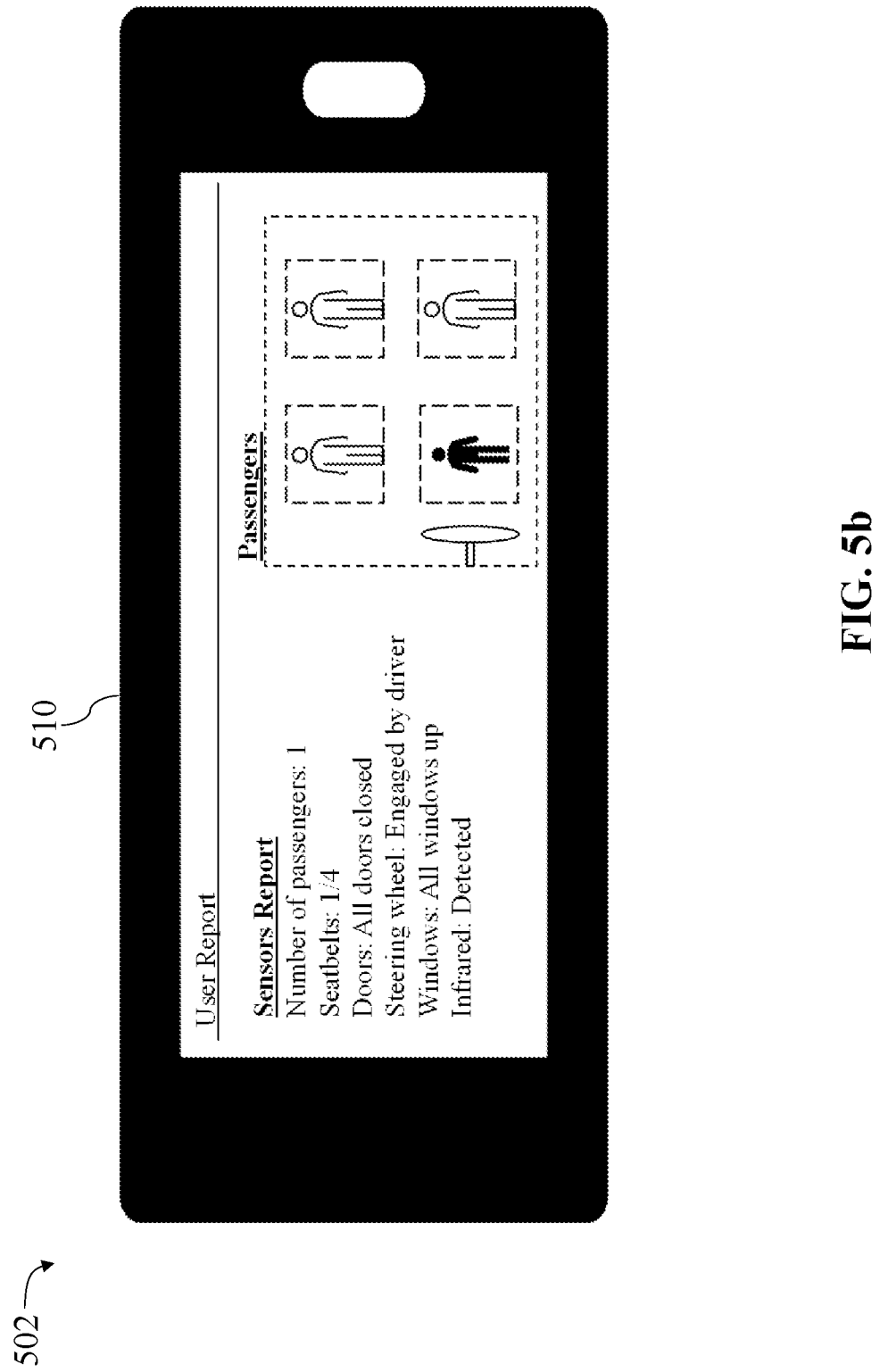
FIG. 5b is another embodiment of a graphical user interface of user report, according to an example embodiment.

Referring now to FIG. 5b, another embodiment of a report 502 illustrated on a graphical display 510 is shown. As illustrated, the report 502 includes a summary of the sensors being used in the system. Furthermore, the report 502 includes a graphical representation of the number of passengers detected in the vehicle. The graphical representation may provide an entertaining experience for the user. The sensor report shows that one passenger is in the vehicle and this is also reflected in the graphical representation. Furthermore, the sensor report shows that one out of four of the seatbelts are in the buckled position, that all doors of the vehicle are closed, that the steering wheel is currently engaged by the driver, that all of the windows are up, and that the infrared signature of a being has been detected.

The report may be displayed inside the vehicle on a graphical display for the user to see and review. Alternatively, the report may be displayed on a remote computing device operated by the user. The report may increase the user's confidence in the sanitary conditions of the vehicle. For instance, the present invention may be used in a variety of applications, such as in personal vehicles and commercial vehicles. Commercial vehicles, such as ride-sharing vehicles (e.g., UBER®, LYFT®), public transportation vehicles, and rental vehicles may require frequent sanitization to ensure safety to the consumer and operator of the vehicle.

In the event that the vehicle is a commercial vehicle, the report may provide the consumer (i.e., the individual obtaining a ride) with confidence about the sanitary conditions of the vehicle. Moreover, the user may be able to anonymously access the report about the sanitary conditions via an application on the user's remote computing device 190. In this way, consumers can make informed decisions about the cleanliness of a vehicle (e.g., deciding to decline a ride from a driver that has an unsanitary vehicle).

Figure 5C:
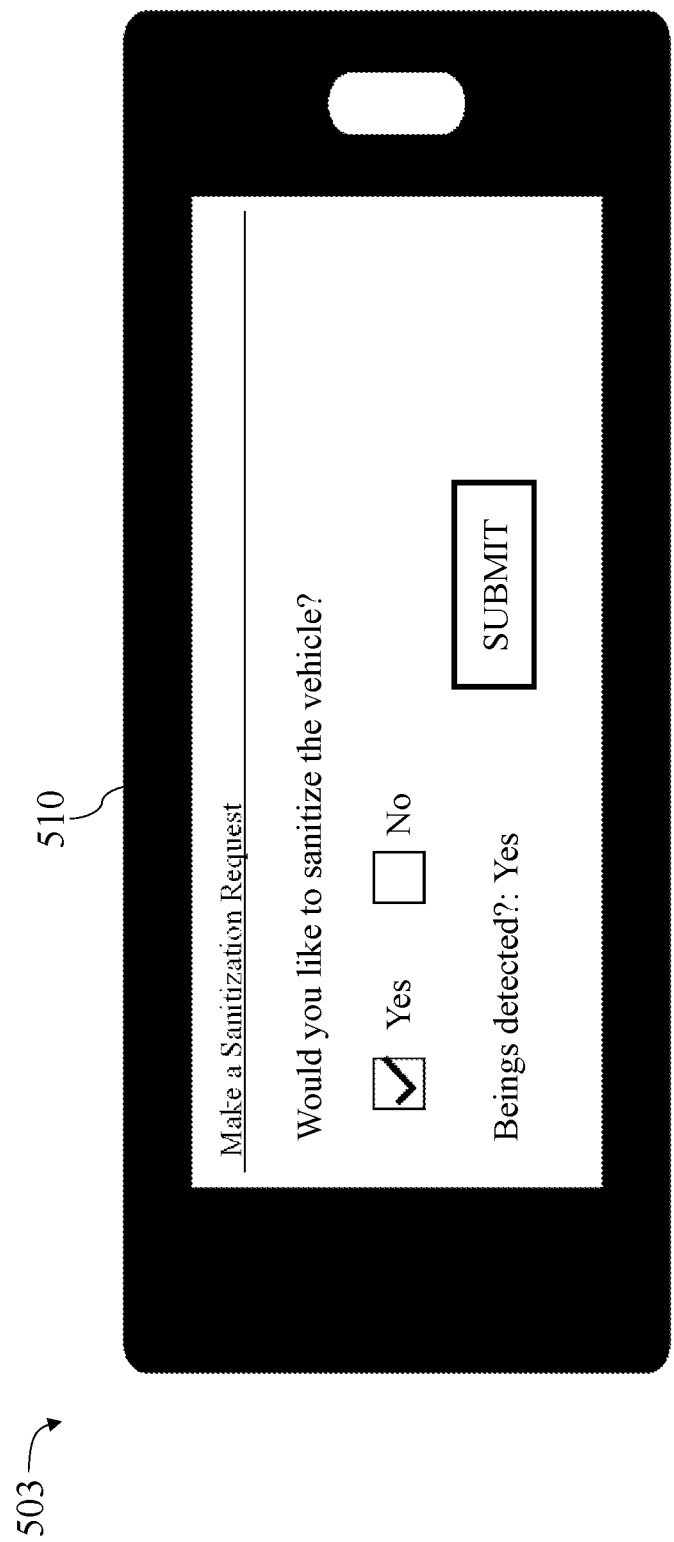
FIG. 5c is an embodiment of a graphical user interface for requesting a sanitization, according to an example embodiment.
Figure 5D:
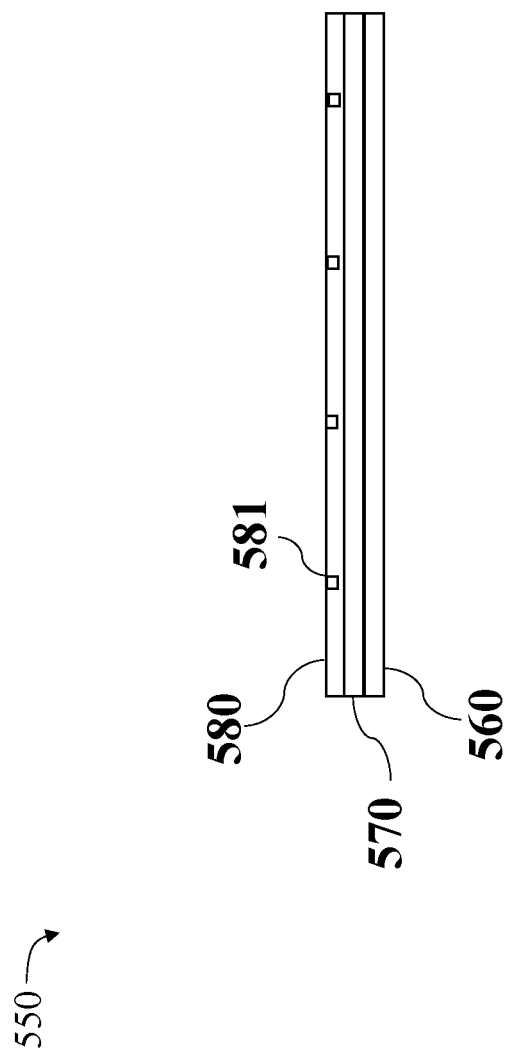
FIG. 5d is a multi-layered window for displaying a user report on the window, according to an example embodiment; and, FIG. 6 is a block diagram of an example computing device and other computing devices, according to an example embodiment.

In one embodiment, a graphical user interface ("GUI") for requesting a sanitization is included. With reference now to FIG. 5c, a graphical user interface for requesting sanitization 503 is shown. As illustrated, the GUI 503 asks the user if they would like to sanitize the vehicle (options: yes/no) and the sanitization can be initiated by pressing the "SUBMIT" button. Moreover, the GUI tells the user whether or not a being has been detected. Various screen gestures may be used to confirm the sanitization. For instance, the "SUBMIT" button may require holding down the button for at least a few seconds to confirm the sanitization. Furthermore, a screen gesture such as sliding the submit button may be used to confirm the sanitization.

ii. Methods

As will be appreciated by those in the art, there is a large variety of conditions that might require sanitization to ensure safety to the user(s) of the vehicle. As addressed above, each sensor (111, 112, 113) used in the being detection system is an input to a function for determining the probability of a presence of beings. In a similar fashion, a variety of conditions may be factored into determining if a sanitization is required. For instance, the time since the most recent sanitization protocol, the duration of beings in the vehicle, and if the number of beings in the vehicle has changed, among others. Regardless, one objective of the present invention is to provide a means to safely sanitize a vehicle and ensure safety of the user. The safety of the user is two-fold: (1) safety from harmful radiation and (2) safety from germs that may be airborne or found on surface(s) inside the vehicle. As described in greater detail below, both safety considerations are addressed by way of the capabilities of the system and the methods for sanitizing the vehicle.

Figure 2A:
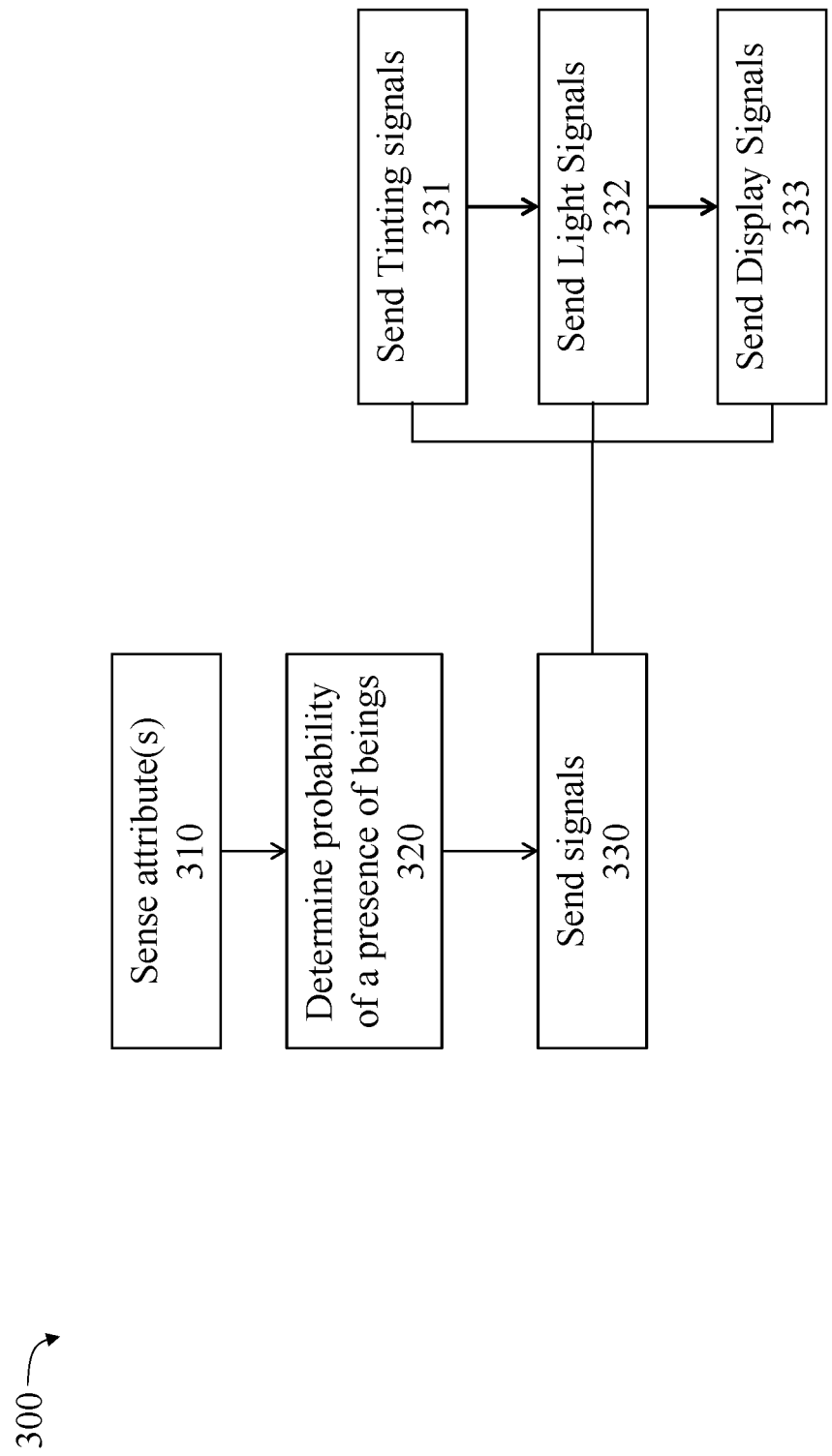
FIG. 2a is a block-flow diagram of a process for treating a vehicle, including sensing attributes, determining a probability of a presence of beings of a vehicle, and sending signals to the appropriate components of the system, according to an example embodiment.
Figure 2B:
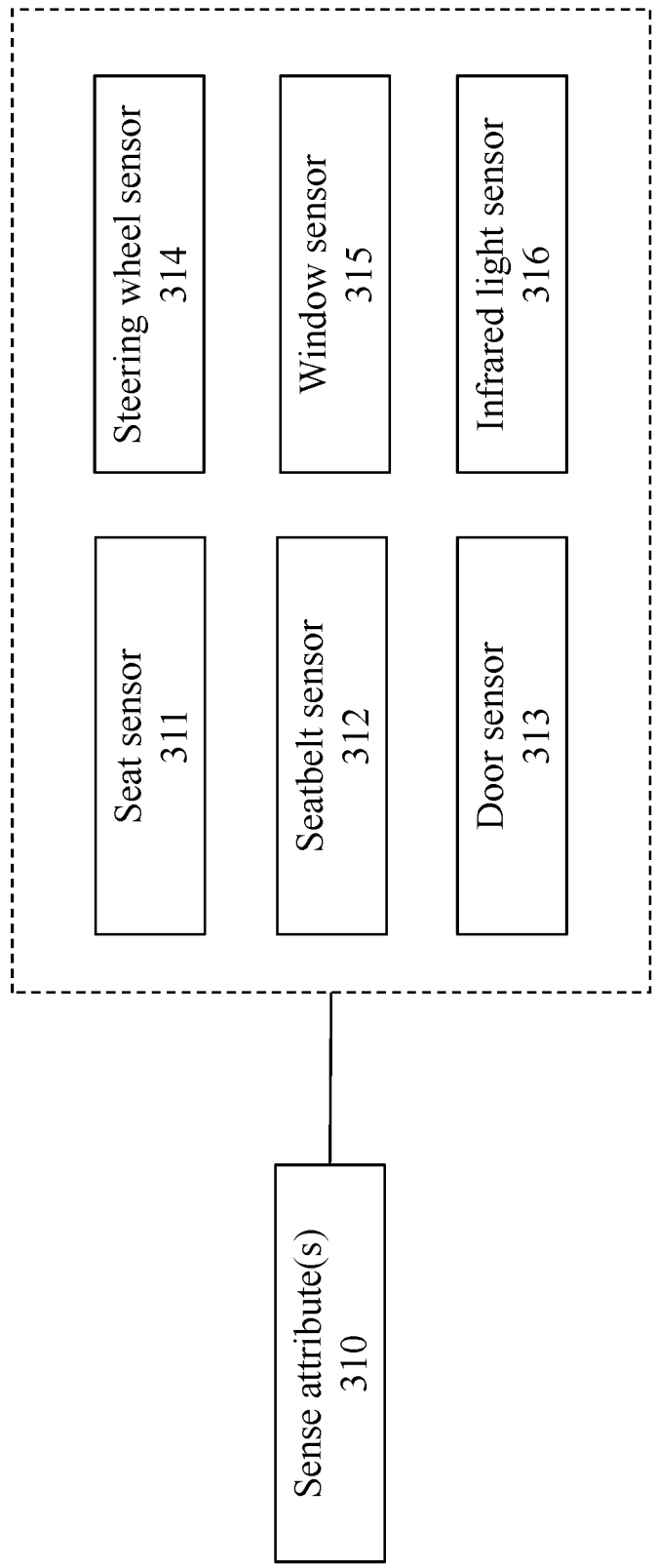
FIG. 2b is a more particular embodiment of an attribute sensing step, according to an example embodiment.

With reference now to FIGS. 2a-2b, a method 300 for treating a vehicle is shown. The method comprises (i) sensing 310 at least one attribute associated with the vehicle using a being detection system, (ii) determining 320 a probability of a presence of beings within the at least one enclosed compartment of the vehicle, and (iii) sending signals 330.

The sensing 310 generally includes using the being detection system. As described in greater detail above, the being detection system may comprise one or more of a seat sensor, a seatbelt sensor, a door sensor, a steering wheel sensor, a daylight sensor, a window sensor, and an infrared light sensor, among other types of sensors. The being detection system, being comprised of a plurality of sensors, is therefore capable of sensing attributes associated with the vehicle via the plurality of sensors. The sensing can be performed continuously, or at timed intervals to reduce the computational load on the processor(s).

The sensing 310 step may include sensing one or more of a seat sensor 311, a seatbelt sensor 312, a door sensor 313, a steering wheel sensor 314, a window sensor 315, and an infrared light sensor 316. The sensing 310 may also including sensing by a daylight sensor (not illustrated).

After the sensing 310, the data provided by the signals from the being detection system may be processed to determine a probability of a presence of beings 320 within the vehicle (e.g., an enclosed compartment). The probability of a presence of beings is represented on a percentage scale (i.e., 0 to 100% probability). Furthermore, the probability of a presence of beings may be a function of the various sensor signals sent by the being detection system. How each sensor signal might modify the probability of a presence of beings is described above. The probability of a presence of beings may be at, above, or below a minimum probability threshold. Above the minimum probability threshold, the system cannot guarantee that a being is not present in the vehicle and consequently will not conduct a sanitizing protocol that may be harmful to the being (e.g., human being). In contradistinction, if the probability of a presence of beings is below a minimum probability threshold, the system can safely conduct a sanitizing protocol that utilizes harmful radiation (e.g., unsafe UV-C light).

While the information presented herein regarding what type of light may be used is binary (i.e., use unsafe light when a being isn't detected, use safe light when a being is detected), any combination of what type is light is used is within the spirit and scope of the invention. For instance, a being detection system may detect a being in the driver seat of a vehicle, while no beings are detected in the rear portion of the vehicle. In such an instance, the system may power-on an unsafe UV-C light in the rear portion of the vehicle (away from the detected being) while a safe UV-C light is powered-on near the detected being. In this way, the methods and systems generally use the being detection system to minimize the risk to any beings in the vehicle by radiation, while simultaneously minimizing the risk of infection (e.g., by airborne or surface-borne germs).

After determining the probability of a presence of beings 320, the method comprises sending signals 330 to the appropriate components of the system. In one embodiment, the sending signals 330 comprises sending tinting signals 331 to a surface tinting means. The tinting signals may adjust a window tinting on at least one window of the vehicle. If the probability of a presence of beings is below a minimum probability threshold, the surface tinting means may adjust the shade to a safe shade. Conversely, if the probability of a presence of beings is above a minimum probability threshold, the surface tinting means may adjust the shade to an unsafe shade.

The sending signals 330 may also comprise sending light signals 332 to a first sanitizing light. If the probability of a presence of beings is below the minimum probability threshold and if the window tinting of the vehicle is a safe shade, the light signals power-on at least one sanitizing light. Conversely, if the probability of a presence of beings is above the minimum probability threshold, the light signals 332 may power-off at least one sanitizing light (e.g., a sanitizing light that emits harmful radiation).

In one embodiment, a method comprises sanitizing the at least one enclosed compartment of the vehicle, where the sanitizing comprises emitting sanitizing radiation from at least the first sanitizing light on one or more surfaces and air within the at least one enclosed compartment. The sanitizing may comprise emitting sanitizing radiation for a time sufficient and an intensity sufficient to eliminate at least 95% of airborne germs (e.g., viruses, bacteria, protozoa). In another embodiment, the sanitizing may comprise emitting sanitizing radiation for a time sufficient and an intensity sufficient to eliminate at least 99% of airborne germs.

In one embodiment, the second sanitizing light is of a second type, wherein sanitizing lights of a first type emit first sanitizing radiation and wherein sanitizing lights of a second type emit second sanitizing radiation. In one embodiment, sanitizing radiation of the first type may include unsafe UV-C radiation, and the second sanitizing radiation includes safe UV-C radiation and excludes unsafe UV-C radiation.

In one embodiment, the method further comprises sending graphical display signals 333, including a report to a graphical display and displaying the report on the graphical display.

Figure 3:
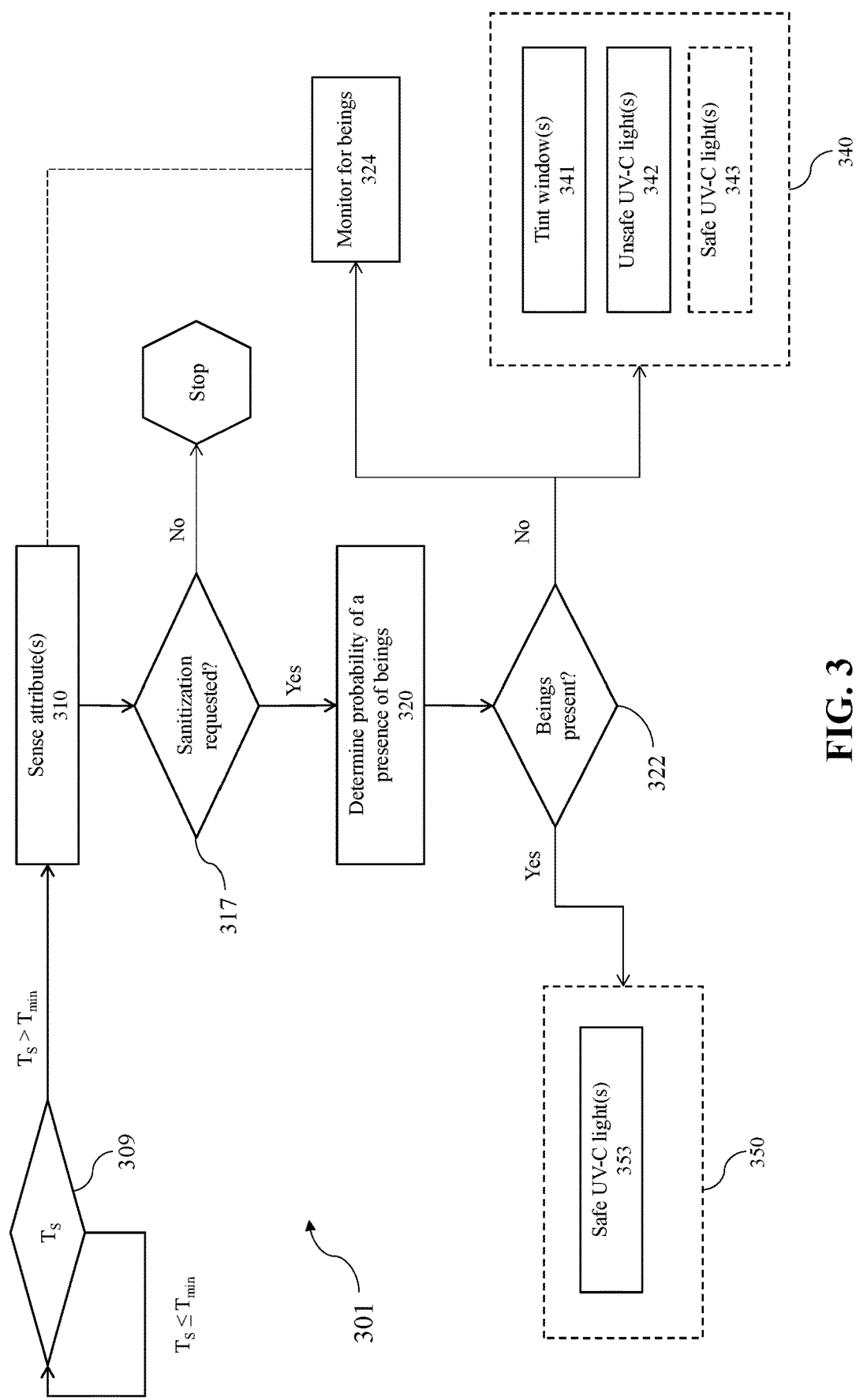
FIG. 3 is a block-flow diagram of a more particular method for treating a vehicle, according to an example embodiment.

With reference now to FIG. 3, an embodiment of a method 301 for detecting a presence of beings and conducting an appropriate sanitizing protocol is shown. Prior to initiating the method, the system tracks time using a timer ($T_S$), until a minimum amount of time since a last sanitization ($T_{min}$) 309 has been reached. Once the amount of time ($T_S$) exceeds the minimum amount of time ($T_{min}$) (i.e., $T_S > T_{min}$), the method is initiated. In this way, a timer may be used to control the frequency of sanitization and efficiently use the system's resources, such as the sanitizing lights and power source in the vehicle.

As illustrated, the method includes the sensing step 310 described above. After the sensing step 310, in one embodiment the system determines if a sanitization protocol should be requested 317. Requesting a sanitization protocol can be determined in a variety of ways. For instance, for efficiency the system should not request a sanitization protocol if no beings have been detected in the vehicle since the last sanitization. A sanitization may be requested, for instance, if a total amount of time beings have been in the vehicle passes a minimum threshold, or if the number of beings who have entered the vehicle has changed, among other characteristics.

Moreover, a user may desire a sanitization (regardless if one is necessary based on the current parameters). The system may provide a GUI an operator to remotely request sanitization (see discussion of FIG. 5c, above). Regardless, if a sanitization is requested at decision 317, the system determines a probability of a presence of beings 320 as described above.

After the determining step 320, a decision is made based on if beings are present 322. The decision 322 is generally decided relative to the specified minimum probability threshold for the probability of a presence of beings. If no beings are detected (e.g., the probability is below the minimum probability threshold), then the method includes monitoring for a presence of beings 324 and conducts a sanitization that utilizes unsafe radiation 340. The monitoring for beings 324 may be continuous (e.g., signals are sent from the being detection system to the processor(s) as fast as possible), or intermittent (e.g., to reduce the computational load on the processor(s)). Regardless, while beings continue to be absent from the vehicle, the system conducts the sanitization that utilizes unsafe radiation 340. The sanitization generally includes tinting the windows 341 to prevent harmful rays from passing through via the surface tinting means, and powering-on the unsafe UV-C light(s) 342. The unsafe UV-C sanitization may optionally include powering-on safe UV-C light(s) 343 (e.g., to speed-up the sanitization, to maximally utilize the sanitizing lights).

If beings are present at the decision 322, then the system conducts a safe sanitization 350. The safe sanitization generally includes powering-on the safe UV-C light(s) 353. Furthermore, the tinting may be adjusted to an unsafe tint if desired (not illustrated).

Following the end of the sanitization protocol, the timer may be reset to zero and begins to count up again until the minimum amount of time has been met. In this way, the system and method provide an automated sanitization system that ensures safety for the user(s).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A method for treating a land-based vehicle having at least one enclosed compartment with radiation, wherein the method comprises:
sensing at least one attribute associated with the land-based vehicle using at least one sensor, wherein the at least one sensor comprises a door sensor; wherein a door of the land-based vehicle comprises an open position and a closed position and has a lock that has a locked state and an unlocked state;
determining, with at least one processor based on data provided by the at least one sensor, a probability of a presence of beings for the at least one enclosed compartment of the land-based vehicle;
sending tinting signals to a surface tinting means; wherein the tinting signals adjust a window tinting on at least one window of the land-based vehicle based on the tinting signals; wherein the window tinting has a shade having a safe shade and an unsafe shade; wherein, if a probability of the presence of beings is below the probability threshold, the surface tinting means adjusts the shade to the safe shade, thereby preventing unsafe UV-C light from passing through the at least one window;
sending light signals to at least one sanitizing light source when the probability of the presence of beings is below the probability threshold and if the shade is the safe shade;
activating the at least one sanitizing light source based on the light signals to emit unsafe UV-C light when the probability of the presence of beings is below the probability threshold and if the shade is the safe shade; and
activating (i) the at least one sanitizing light source, based on the light signals, to emit safe UV-C light when the probability of the presence of beings is above the probability threshold and if the shade is the unsafe shade, and (ii) stopping the at least one sanitizing light source from emitting unsafe UV-C light;
if the at least one sanitizing light source is activated, then unlocking the land based vehicle (i) causes a modification to the probability of the presence of beings to be above the probability threshold, and (ii) halts any emittance of unsafe UV-C light.

2. The method of claim 1, wherein the method comprises:
sending graphical display signals to a graphical display, wherein the graphical display signals include a report; and
displaying the report on the graphical display.

3. The method of claim 1, wherein the method comprises sanitizing the at least one enclosed compartment of the land-based vehicle, wherein the sanitizing comprises emitting sanitizing radiation from the at least one sanitizing light source on one or more surfaces and air within the at least one enclosed compartment.

4. The method of claim 1, wherein the sending the light signals comprises sending the light signals to:
a first sanitizing light source of the at least one sanitizing light source, wherein the first sanitizing light source is of a first type of radiation such that it emits a first sanitizing radiation; and
a second sanitizing light source of the at least one sanitizing light source, wherein the second sanitizing light source is of a second type of radiation such that it emits a second sanitizing radiation.

5. The method of claim 4, wherein the first sanitizing radiation includes unsafe UV-C radiation, and wherein the second sanitizing radiation includes safe UV-C radiation and excludes the unsafe UV-C radiation.

6. The method of claim 1, further comprising modifying the probability of the presence of beings within the at least one enclosed compartment based on plurality of sensor signals from the at least one sensor.

* * * * *